(12) United States Patent
Roby

(10) Patent No.: US 6,206,908 B1
(45) Date of Patent: Mar. 27, 2001

(54) ABSORBABLE POLYMER AND SURGICAL ARTICLES FABRICATED THEREFROM

(75) Inventor: Mark S. Roby, Kilingworth, CT (US)

(73) Assignee: United States Surgical Corporation, Norwalk, CT (US)

(*) Notice: Subject to any disclaimer, the term of this patent is extended or adjusted under 35 U.S.C. 154(b) by 0 days.

(21) Appl. No.: 09/304,488

(22) Filed: May 3, 1999

Related U.S. Application Data

(63) Continuation-in-part of application No. 09/173,500, filed on Oct. 16, 1998, now abandoned, which is a continuation-in-part of application No. 08/730,200, filed on Oct. 15, 1996, now abandoned, which is a continuation-in-part of application No. 08/307,954, filed on Jun. 16, 1994, now abandoned.

(51) Int. Cl.$^7$ .............................. A61B 17/04; C08G 63/08

(52) U.S. Cl. ...................... 606/228; 606/230; 528/354; 528/357; 525/408; 525/415; 525/411

(58) Field of Search .................................. 606/228, 230; 525/408, 411, 415; 528/354, 357

(56) References Cited

U.S. PATENT DOCUMENTS

| | | | |
|---|---|---|---|
| 2,668,162 | 2/1954 | Lowe | 260/78.3 |
| 2,683,136 | 7/1954 | Higgins | 260/78.3 |
| 2,703,316 | 3/1955 | Schneider | 260/78.3 |
| 2,758,987 | 8/1956 | Salzberg | 260/78.3 |
| 3,225,766 | 12/1965 | Baptist et al. | 128/335.5 |
| 3,268,486 | 8/1966 | Kloowijk | 260/78.3 |
| 3,268,487 | 8/1966 | Klootwijk | 260/78.3 |
| 3,297,033 | 1/1967 | Schmitt et al. | 128/335.5 |
| 3,422,181 | 1/1969 | Chirgwin, Jr. | 264/345 |
| 3,442,871 | 5/1969 | Schmitt et al. | 260/78.3 |
| 3,463,158 | 8/1969 | Schmitt et al. | 128/334 |
| 3,468,853 | 9/1969 | Schmitt et al. | 260/78.3 |
| 3,531,561 | 9/1970 | Trehu | 264/210 |
| 3,565,869 | 2/1971 | DeProspero | 260/78.3 |
| 3,597,449 | 8/1971 | DeProspero et al. | 260/340.2 |
| 3,620,218 | 11/1971 | Schmitt et al. | 128/334 R |
| 3,626,948 | 12/1971 | Glick et al. | 128/335.5 |
| 3,636,956 | 1/1972 | Schneider | 128/335.5 |
| 3,733,919 | 5/1973 | Rupp, II | 74/242.16 |
| 3,736,646 | 6/1973 | Schmitt et al. | 29/458 |
| 3,739,773 | 6/1973 | Schmitt et al. | 128/92 BC |
| 3,772,420 | 11/1973 | Glick et al. | 264/102 |
| 3,781,349 | 12/1973 | Ramsey et al. | 260/535 P |
| 3,784,585 | 1/1974 | Schmitt et al. | 260/861 |
| 3,792,010 | 2/1974 | Wasserman et al. | 260/32.2 R |
| 3,797,499 | 3/1974 | Schneider | 128/334 R |
| 3,839,297 | 10/1974 | Wasserman et al. | 260/78.3 R |
| 3,846,382 | 11/1974 | Ramsey et al. | 260/78.3 R |
| 3,867,190 | 2/1975 | Schmitt et al. | 117/138.8 A |
| 3,878,284 | 4/1975 | Schmitt et al. | 264/184 |
| 3,896,802 | 7/1975 | Williams | 128/156 |

(List continued on next page.)

FOREIGN PATENT DOCUMENTS

| | | |
|---|---|---|
| 0600237 | 6/1994 | (EP) . |
| 0654549 | 5/1995 | (EP) . |
| 779291 | 7/1957 | (GB) . |
| 1332505 | 10/1973 | (GB) . |
| 1414600 | 11/1975 | (GB) . |
| 2102827 | 2/1983 | (GB) . |

OTHER PUBLICATIONS

D.K. Gilding, et al, "Biodegradable Polymers for Use in Surgery—Polyglycolic/poly (actic acid) homo–and copolymers: 1" Polymer, vol. 20, pp. 1459–1464 (1979).

D.F. Williams (ed.) Biocompatibilityof Clinical Implant Materials, vol. 11, Chapter 9: "Biodegradable Polymers" (1981).

Primary Examiner—Gary Jackson

(57) ABSTRACT

Absorbable copolymers are fabricated from the random polymerization of 1,4 dioxane-2-one and 1,3 dioxane-2-one monomers. The copolymers are useful in forming surgical articles, including both monofilament and multifilament sutures.

4 Claims, 2 Drawing Sheets

U.S. PATENT DOCUMENTS

| | | | |
|---|---|---|---|
| 3,902,497 | 9/1975 | Casey | 128/296 |
| 3,937,223 | 2/1976 | Roth | 128/325 |
| 3,982,543 | 9/1976 | Schmitt et al. | 128/335.5 |
| 3,987,937 | 10/1976 | Coucher | 222/193 |
| 4,033,938 | 7/1977 | Augurt et al. | 260/78.3 R |
| 4,045,418 | 8/1977 | Sinclair | 260/78.3 R |
| 4,052,988 | 10/1977 | Doddi et al. | 128/335.5 |
| 4,057,537 | 11/1977 | Sinclair | 260/78.3 R |
| 4,060,089 | 11/1977 | Noiles | 128/325 |
| 4,137,921 | 2/1979 | Okuzumi et al. | 128/335.5 |
| 4,157,437 | 6/1979 | Okuzumi et al. | 528/354 |
| 4,243,775 | 1/1981 | Rosensaft et al. | 525/415 |
| 4,246,904 | 1/1981 | Kaplan | 128/335.5 |
| 4,273,920 | 6/1981 | Nevin | 528/361 |
| 4,275,813 | 6/1981 | Noiles | 206/339 |
| 4,279,249 | 7/1981 | Vert et al. | 128/92 D |
| 4,300,565 | 11/1981 | Rosensaft et al. | 128/335.5 |
| 4,429,080 | 1/1984 | Casey et al. | 525/415 |
| 4,643,191 | 2/1987 | Bezwada et al. | 128/335.5 |
| 4,653,497 | 3/1987 | Bezwada et al. | 128/335.5 |
| 4,705,820 | 11/1987 | Wang et al. | 524/381 |
| 4,744,365 | 5/1988 | Kaplan et al. | 128/335.5 |
| 4,788,979 | 12/1988 | Jarrett et al. | 128/335.5 |
| 4,791,929 | 12/1988 | Jarrett et al. | 128/335.5 |
| 4,838,267 | 6/1989 | Jamiolkowski et al. | 128/335.5 |
| 4,891,263 | 1/1990 | Kotliar et al. | 428/225 |
| 4,916,193 | 4/1990 | Tang et al. | 525/413 |
| 4,916,207 | 4/1990 | Boyle, Jr. et al. | 528/370 |
| 4,920,203 | 4/1990 | Tang et al. | 525/409 |
| 4,965,300 | 10/1990 | Eichenauer et al. | 525/415 |
| 5,007,923 | 4/1991 | Bezwada et al. | 606/231 |
| 5,037,950 | 8/1991 | Bezwada et al. | 528/354 |
| 5,047,048 | 9/1991 | Bezwada et al. | 606/231 |
| 5,066,772 | 11/1991 | Tang et al. | 528/354 |
| 5,080,665 | 1/1992 | Jarrett et al. | 606/219 |
| 5,120,802 | 6/1992 | Mares et al. | 525/415 |
| 5,133,739 | 7/1992 | Bezwada et al. | 606/230 |
| 5,145,945 | 9/1992 | Tang et al. | 528/370 |
| 5,147,399 | 9/1992 | Dellon et al. | 623/12 |
| 5,152,781 | 10/1992 | Tang et al. | 606/230 |
| 5,185,408 | 2/1993 | Tang et al. | 525/415 |
| 5,225,520 | 7/1993 | Kennedy et al. | 528/354 |
| 5,236,444 | 8/1993 | Muth et al. | 606/230 |
| 5,252,701 | 10/1993 | Jarrett et al. | 528/354 |
| 5,314,989 | 5/1994 | Kennedy et al. | 528/354 |
| 5,322,925 | 6/1994 | Muth et al. | 528/354 |
| 5,354,298 | 10/1994 | Lee et al. | 606/72 |
| 5,359,831 | 11/1994 | Brown et al. | 53/430 |
| 5,391,707 | 2/1995 | Jiang | 528/354 |
| 5,403,347 | 4/1995 | Roby et al. | 606/230 |
| 5,611,986 | * 3/1997 | Datta et al. | 264/328.16 |

* cited by examiner

ABSORBABLE POLYMER AND SURGICAL ARTICLES FABRICATED THEREFROM

RELATED APPLICATIONS

This application is a continuation-in-part of application Ser. No. 09/173,500 filed Oct. 16, 1998, now abandoned which is a continuation-in-part of application Ser. No. 08/730,200 filed Oct. 15, 1996, now abandoned, which is a continuation-in-part of application Ser. No. 08/307,954 filed Sep. 16, 1994, now abandoned.

TECHNICAL FIELD

Absorbable copolymers fabricated from the random copolymerization of 1,4 dioxane-2-one and 1,3 dioxane-2-one monomers, and more particularly surgical articles made totally or in part therefrom, including both monofilament and multifilament sutures are provided.

BACKGROUND

Polymers and copolymers of, and surgical devices made from lactide and/or glycolide and/or related compounds are well-known. See, e.g., U.S. Pat. Nos. 2,668,162, 2,683,136, 2,703,316, 2,758,987, 3,225,766, 3,268,486, 3,268,487, 3,297,033, 3,422,181, 3,442,871, 3,463,158, 3,468,853, 3,531,561, 3,565,869, 3,597,449, 3,620,218, 3,626,948, 3,636,956, 3,736,646, 3,739,773, 3,772,420, 3,733,919, 3,781,349, 3,784,585, 3,792,010, 3,797,499, 3,839,297, 3,846,382, 3,867,190, 3,987,937,, 3,878,284, 3,896,802, 3,902,497, 3,937,223, 3,982,543 4,033,938, 4,045,418, 4,057,537, 4,060,089, 4,137,921, 4,157,437, 4,243,775, 4,246,904, 4,273,920, 4,275,813, 4,279,249, 4,300,565, and 4,744,365, U.K. Pat. or Appln. Nos. 779,291, 1,332,505, 1,414,600 and 2,102,827, D. K. Gilding et al., "Biodegradable polymers for-use in surgery-polyglycolic/poly (lactic acid) homo-and copolymers: 1, "*Polymer*, Volume 20, pages 1459–1464 (1979), and D. F. Williams (ed.) *Biocompatibility of Clinical Implant Materials*, Volume II, chapter 9: "Biodegradable Polymers" (1981).

Surgical devices prepared from copolymers containing dioxanone and polycarbonates are also known in the art. For example, U.S. Pat. No. 4,052,988 describes random copolymers containing dioxanone and up to 50 percent by weight of other copolymerizable monomers which produce non-toxic and absorbable copolymers.

As another example, U.S. Pat. No. 5,037,950 describes copolymers having sequential units of rho-dioxanone and sequential units of either tetramethylene carbonate, pentamethylene carbonate, hexamethylene carbonate, heptamethylene carbonate, octamethylene carbonate, nonamethylene carbonate, decamethylene carbonate, undecamethylene carbonate, and dodecamethylene carbonate, with hexamethylene carbonate being preferred. The '950 patent describes neither random copolymers nor copolymers containing trimethylene carbonate.

As yet a further example, U.S. Pat. No. 5,145,945 generically describes random copolymers of trimethylene carbonate and dioxanones other than carbonates. In addition, see U.S. Pat. Nos. 4,891,263; 4,916,193; 4,902,203; and 5,152,781.

As described above bioabsorbable sutures are known in the art. However, in the manufacture of sutures an important characteristic of a suture is the amount of effort typically required to straighten the suture upon its removal from the package in order to ready the suture for use. This effort appears to be related to the "strain energy" of the suture, i.e., the integration of the stress-strain curve for the suture measured in kilogram-mm, and is equivalent to the work expended in elongating the monofilament by a specified percentage of its original length. As the strain energy of a given size of suture decreases so, too, does the amount of effort required to straighten the suture prior to use. A decrease in strain energy also appears to relate to the perceived flexibility of the suture.

Therefore, it would be advantageous to provide a bioabsorbable suture which exhibits a desired absorption profile and improved flexibility and handling characteristics when compared to commercially available sutures having the same absorption profile, while maintaining other desired properties, such as knot-pull strength and straight-pull retention.

SUMMARY

It has now been found that absorbable surgical articles may be formed from the random copolymerization of 1,4 dioxane-2-one and 1,3 dioxane-2-one. Preferably, copolymers useful in forming surgical articles in accordance with the present disclosure include copolymers comprising a predominant component of dioxanone. A "predominant component" is a component which is present is an amount greater than 50 percent.

In a particularly useful embodiment these block copolymers of may be spun into fibers. The fibers can be fabricated into both monofilament and braided multifilament sutures. Preferably copolymers useful in this embodiment include at least about 60 mole percent dioxanone, the remainder being trimethylene carbonate.

There is also provided a process for manufacturing a suture exhibiting excellent flexibility and/or increased knot performance for a given size comprising the operations of extruding the block copolymer at an extrusion temperature of from about 80° C. to about 140° C. to provide a monofilament fiber, stretching the solidified monofilament at a temperature of from about 30° C. to about 60° C. in water (or other suitable liquid medium such as for example glycerol) or at from about 30° C. to about 95° C. in air (or other suitable gaseous medium) at a stretch ratio of from about 3:1 to about 10:1 to provide a stretched monofilament. The stretched monofilament preferably is then frozen at a temperature of from about –25° C. to about 0° C. The suture then may be annealed with or without relaxation at a temperature of from about 40° C. to about 95° C. to provide the finished suture.

DESCRIPTION OF THE PREFERRED EMBODIMENTS

Figure 1A:
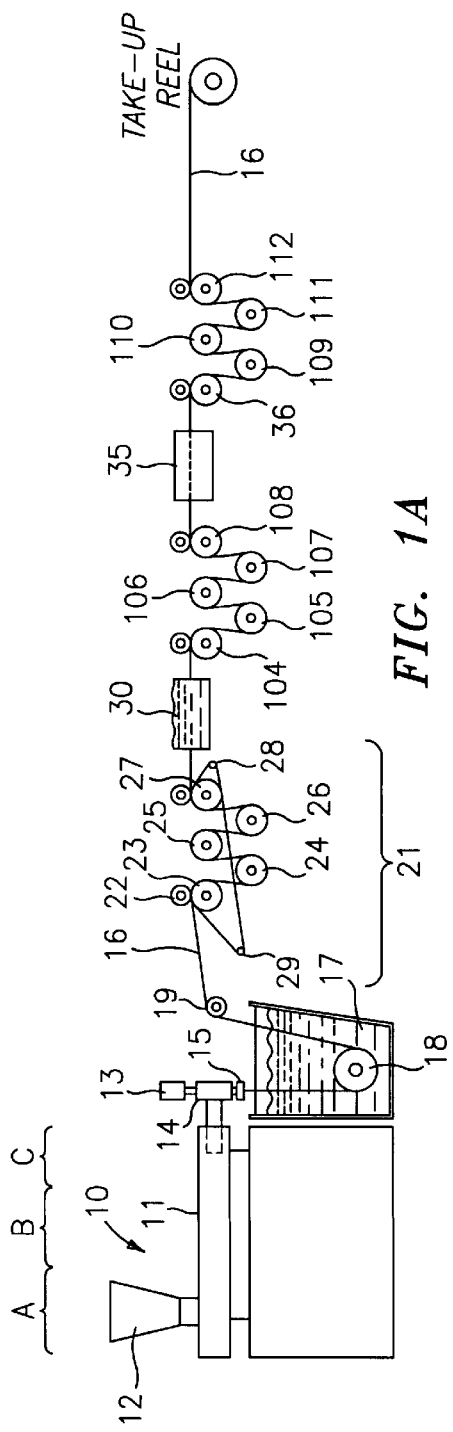
FIG. 1A is a schematic illustration of an apparatus which is suitable for manufacturing the monofilament suture in accordance with this disclosure; and, FIG. 1B is a modification of the apparatus of FIG. 1A which is particularly suitable for manufacturing the monofilament sutures of the present disclosure of smaller size, e.g., sizes 3/0 and smaller.

It has been found that monomers of 1,3 dioxane-2-one and 1,4 dioxane-2-one (with 1,4 dioxane-2-one as the predominant component thereof) can advantageously be randomly copolymerized to form a copolymer useful in forming surgical sutures.

Such random copolymers include copolymers having at least 50 mole percent 1,4 dioxane-2-one. Preferably, 1,4 dioxane-2-one makes up at least about 60 mole percent of the copolymer. Most preferably, 1,4 dioxane-2-one comprises at least about 80 percent of the copolymer, with about 93 mole percent being preferred. The 1,4 dioxane-2-one may be copolymerized with any soft phase forming monomer, with trimethylene carbonate being preferred. These copolymers can be synthesized by known methods. See, for example, U.S. Pat. Nos. 4,653,497; 4,838,267; 4,605,730; and 4,788,979 the disclosures of which are incorporated herein by reference. Such copolymers of 1,3 dioxane-2-one and 1,4 dioxane-2-one have a molecular weight such that they exhibit an inherent viscosity of from about 1.2 to about 2.5 dl/g measured at 30° C. and a concentration of 0.25 g/dl in hexafluoroisopranol (HFIP) are useful.

Although it is preferred to fabricate surgical sutures from these copolymers, a wide variety of surgical articles can be manufactured from the copolymers disclosed herein. These include but are not limited to clips and other fasteners, staples, sutures, pins, screws, prosthetic devices, wound dressings, drug delivery devices, anastomosis rings, and other implantable devices. Fibers made from the copolymers of this invention can be knitted or woven with other fibers, either absorbable or nonabsorbable to form meshes or fabrics. The copolymers herein can also be used as an absorbable coating for surgical devices. The copolymers of this invention can be formed into surgical articles using any known technique, such as, for example, extrusion, molding and/or solvent casting. The copolymers can be used alone, blended with other absorbable compositions, or in combination with non-absorbable components.

Multifilament sutures of the present invention may be made by methods known in the art. Braid constructions such as those disclosed and claimed in U.S. Pat. Nos. 5,059,213 and 5,019,213 are suitable for the present multifilament sutures.

A suitable process for the manufacture of monofilament sutures includes the operations of melt extruding the resin at an extrusion temperature of from about 80° C. to about 140° C. to provide a monofilament, stretching the solidified monofilament at a temperature of from about 30° C. to about 60° C. in water (or other suitable liquid-medium) or at from about 25° C. to about 95° C. in nitrogen (or other suitable gaseous medium) at a stretch ratio of from about 3:1 to about 10:1 to provide a stretched monofilament.

Optionally, the solidified monofilament may be stretched at least once in air or other suitable gaseous medium preferably at about 70° C. Preferably, the monofilament is then frozen at a temperature of from about −25° C. to about 0° C. The suture may then be annealed at a temperature of from about 40° C. to about 95° C. to provide the finished suture.

FIG. 1A schematically illustrates a monofilament suture manufacturing operation which is especially suitable for producing larger size sutures, e.g., those of sizes 2/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resins are introduced to the extruder through hopper 12. Any of the copolymers described in this application which are useful for the formation of fibers can be used herein. Optionally, about 0.01 to about 0.1 percent by weight of a plasticizer such as calcium stearate may be added along with the copolymer to extruder 10.

Motor-driven metering pump 13 delivers melt extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 10 cm. If desired, a chimney (not shown), or shield, can be provided to isolate monofilament 16 from contact with air currents which might other-wise affect the cooling of the monofilament in an unpredictable manner. In general, barrel zone A of the extruder can be maintained at a temperature of from about 80° C. to 105° C., zone B at from about 100° C. to 105° C. and zone C at from about 100° C. to about 110° C. Additional temperature parameters include: metering pump block 13 at from about 100° C. to about 110° C. spin pack 14 at from about 100° C. to about 120° C., spinneret 15 at from about 95° C. to about 120° C. and quench bath at from about 10° C. to about 30° C.

Monofilament 16 is passed through quench bath 17 around driven roller 18 and over idle roller 19. Optionally, a wiper (not shown) may remove excess water from the monofilament as it is removed from quench bath 17. On exiting the quench bath the monofilament enters first godet station generally indicated at 21.

First godet station 21 is equipped with five individual godets around which monofilament 16 is wrapped. First godet 23 is provided with nip roll 22 to prevent slippage which might otherwise result. Upon entering first godet station 21, monofilament 16 passes over first godet 23, under second godet 24, over third godet 25, under fourth godet 26 and over fifth godet 27. Fifth godet 27 is proximally located to separation roller 28 which is provided with a plurality of laterally spaced circumferential grooves which act as guides for monofilament 16. After monofilament 16 passes over fifth godet 27 it wraps around a groove on separation roller 28 and extends back to and around a corresponding groove on separation roller 29 located proximal to first godet 23. Monofilament 16 wraps around separation roller 29, ascends up to first godet 23 and continues onward to the remaining godets in the manner just described. When the monofilament passes over the fifth godet 27 a second time, it may he wrapped around a second groove on separation roller 28. The monofilament then extends back to separation roller 29 and around a corresponding groove thereon. The monofilament may pass through first godet station 21 any desired number of times. The solidified monofilament is thus allowed to dwell at ambient conditions before the monofilament enters heating unit 30. In this fashion monofilament 16 is aged or exposed to ambient conditions for a desired period of time prior to being stretched.

It is to be understood that aging or exposing the monofilament to ambient conditions for a predetermined period of time prior to drawing the monofilament can be accomplished in many different ways. For example, any number of godets may be employed to provide the dwell period. In addition, the arrangement of the godets can be varied. Also, other structure suitable for providing aging of the monofilament prior to stretching will be apparent to those skilled in the art.

Monofilament 16 passing from godet 27 is stretched, e.g., with stretch ratios on the order of from about 2:1 to about 7:1 and preferably from about 3:1 to about 5:1, to effect its orientation and thereby increase its tensile strength. Stretching may be achieved by drawing the monofilament at ambient temperatures or drawing the monofilament while or after it has been heated.

In the stretching operation shown in FIG. 1A, generally suitable for larger size sutures, e.g., sizes 2 to 2/0, monofilament 16 is drawn through hot glycerol or hot water (or other suitable liquid medium) draw bath 30 by means of godets 104, 105, 106, 107 and 108 or any other suitable arrangement of godets which rotate at a higher speed than godet station 21 to provide the desired stretch ratio. The temperature of hot water draw bath 30 is advantageously from about 30° C. to about 60° and preferably is from about 40° to about 50°.

Figure 1B:
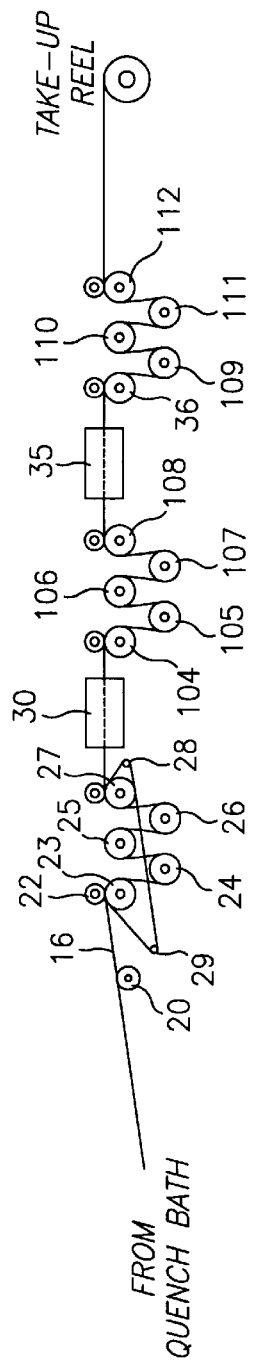

In the alternative stretching operation shown in FIG. 1B, generally preferred for smaller sutures sizes, e.g., sizes 3/0 to 8/0, monofilament 16 is drawn by godets 104, 105, 106, 107, and 108 or any other suitable godet arrangement through hot air convection oven chamber 30, at a temperature of from, about 30° C. to about 95° C. and preferably from about 40° C. to about 60° C. to provide the desired amount of stretch. Following the stretching operation shown in FIG. 1A or 1B, monofilament 16 optionally may be subjected to an on-line annealing and/or additional stretching without shrinkage or relaxation with shrinkage operation as a result of which the monofilament shrinks. In the processes of FIGS. 1A and 1B, on line annealing with or without relaxation when desired is accomplished by driving monofilament 16 by godets 36, 109, 110, 111, and 112 or any other suitable godet arrangement through second hot air oven chamber 35 at a temperature of from about 40° C. to about 95° C. and preferably from about 50° C. to about 80° C. During the relaxation process, at these temperatures, monofilament 16 will generally recover to within about 80 to about 98 percent, and preferably to within about 90 percent, of its preannealed length to provide the finished suture. For relaxation, the third godet station rotates at a slower speed than the second godet station thus relieving tension on the filament.

Annealing of the suture also may be accomplished without shrinkage of the suture. In carrying out the annealing operation, the desired length of suture may be wound around a creel and the creel placed in a heating cabinet maintained at the desired temperature, e.g. about 40° C. to about 95° C., as described in U.S. Pat. No. 3,630,205. After a suitable period of residency in the heating cabinet, e.g,, about 6 hours or so, the suture will have undergone essentially no shrinkage. As shown in U.S. Pat. No. 3,630,205, the creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then-ready to be packaged and sterilized.

Figure 2:
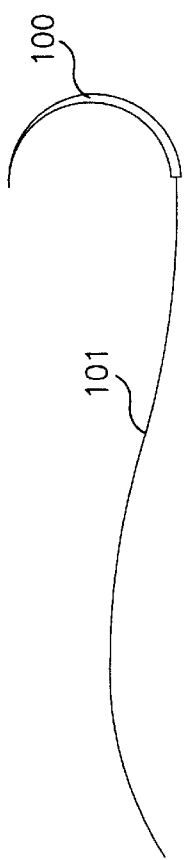
FIG. 2 is a perspective view of a suture of the present disclosure attached to a needle.

The suture of the present disclosure, suture 101, may be attached to a surgical needle 100 as shown in FIG. 2 by methods well known in the art. Wounds may be sutured by passing the needled suture through tissue to create wound closure. The needle preferably is then removed from the suture and the suture tied.

It is further within the scope of this disclosure to incorporate one or more medico-surgically useful substances into the present articles, e.g., substances which accelerate or beneficially modify the healing process when particles are applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye the sutures in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, sutures in accordance with this disclosure are dyed by adding up to about a few percent and preferably about 0.2% dye, such as D&C Violet No. 2 to the resin prior to extrusion.

EXAMPLE 1

1,3 dioxane-2-one (750 grams) and 1,4 dioxane-2-one (4250 grams) are added to a reactor along with 1.0 grams of stannous chloride and 1 gram of diethylene glycol. The mixture is heated and placed at 100° C., with stirring under a nitrogen atmosphere for 25 hours. The temperature is then reduced to 90° C. and stirring continued for 5 hours. The 1,3 dioxane-2-one/1,4 dioxane-2-one copolymer is then sampled.

The reaction product is isolated, comminuted, and treated to remove residual reactants using known techniques. The copolymer is then heated under vacuum to remove residual water, residual solvent, and/or unreacted monomer.

EXAMPLE 2

1,3 dioxane-2-one (750 grams) and 1,4 dioxane-2-one (4250 grams) are added to a reactor along with 0.5 grams of stannous chloride and 1 gram of diethylene glycol. The mixture is heated and placed at 100° C., with stirring under a nitrogen atmosphere for 24 hours. The temperature is then reduced to 90° C. and stirring continued for 8 hours, followed by stirring for 1 hour at 150° C., and stirring for 15 hours at 90° C. The 1,3 dioxane-2-one/1, 4 dioxane-2-one copolymer is then sampled.

The reaction product is isolated, comminuted, and treated to remove residual reactants using known techniques. The copolymer is then heated under vacuum to remove residual water, residual solvent, and/or unreacted monomer.

Table I below sets forth typical conditions for extruding, stretching size 3/0 of sutures from the resins of Example 1 and Example 2, respectively. About 0.05 weight percent of calcium stearate was mixed in the extruder with the resins prior to extrusion in both Examples 1 and 2. After the extrusion operation a monofilament from the resin of Example 1 is placed around the separation rollers and thereafter twelve passages are made around the godets in the first godet station prior to passage in the heating unit. This provides a dwell time of about 10 minutes. The extrusion, stretching, freezing and annealing conditions are as follows:

TABLE 1

CONDITIONS OF MANUFACTURING
SIZE 3/0 OF MONOFILAMENT

| Example | 1 | 2 |
|---|---|---|
| Suture Size | 3/0 | 3/0 |
| Process Conditions | Extrusion | Operation |
| extruder screw, rpm | 1.5 | 0.8 |
| pump rpm | 4.7 | 7.3 |
| barrel temp., ° C., zone A | 103 | 90 |
| barrel temp., ° C., zone B | 106 | 105 |
| barrel temp., ° C., zone C | 107 | 107 |
| clamp temp., ° C. | 107 | 107 |
| adapter temp., ° C. | 107 | 120 |
| pump temp., ° C. | 107 | 107 |
| block temp., ° C. | 107 | 132 |
| barrel melt temp., ° C. | 104 | 105 |
| pump melt temp., ° C. | 102 | 117 |
| spinneret melt temp., ° C. | 97 | 117 |
| barret pressure, psi | 850 | 790 |
| pump pressure, psi | 500 | 500 |
| spinneret pressure, psi | 1600 | 3810 |
| pump size, cc per revolution | 0.297 | 0.160 |
| diameter of spinneret, orifices, mm | 1.25 | 1.25 |
| no. of spinneret orifices | 1 | 1 |
| quench bath temp., ° C. | 25 | 25 |
| Stretching (Orienting) Operation | | |
| draw oven temp., ° C. | 45 | 48 |
| first godet station, mpm | 3.2 | 2.7 |
| second godet station, mpm | 12.4 | 14.2 |
| second oven temp., ° C. | 65 | 80 |
| third godet station, mpm | 20.7 | 17.3 |
| draw ratio | 6.5:1 | 6.5:1 |
| Freezing Operation | | |
| temp., ° C. | −15 | −15 |
| time (hrs.) | 48 | 24 |
| Annealing Operation | | |
| oven temp., ° C. | 80 | 80 |
| time (hrs.) | 6 | 6 |
| Relaxation Operation | | |
| shrinkage, % | 0 | 10 |

The average physical properties of the sutures and the procedures employed for their measurement are set forth in Table II as follows:

TABLE II

PROCEDURES FOR MEASURING PHYSICAL PROPERTIES
OF MONOFILAMENT SUTURES OF THE PRESENT INVENTION

| Physical Property | Test Procedure |
|---|---|
| knot-pull strength, kg | U.S.P. XXI, tensile strength, sutures (881) |
| straight-pull strength, kg | ASTM D-2256, Instron Corporation |
| elongation, % | ASTM D-2256 |
| tensile strength, kg/mm$^2$ | ASTM D-2256, Instron Corporation Series IX Automated Materials Testing System 1.03A |

TABLE II-continued

PROCEDURES FOR MEASURING PHYSICAL PROPERTIES
OF MONOFILAMENT SUTURES OF THE PRESENT INVENTION

| Physical Property | Test Procedure |
|---|---|
| 0–5% and 0–10% strain energies, kg-mm; | ASTM D-2256, Instron Corporation Series IX Automated Materials Testing System 1.03A |

Measurements of knot pull, percent elongation, tensile strength and strain energy were carried out employing an Instron Corporation (Canton, Mass.) Tensile Tester, model no. 1122, equipped with yarn grips and operated with a gauge length of 127 mm and a crosshead speed of 127 mm/min and 51 mm/min for straightpull and knot-pull, respectively. The physical properties of monofilament sutures produced in accordance with the conditions of Table I were measured at 21° C. and 50 percent relative humidity.

Table III below sets forth the physical properties of the size 3/0 suture of Examples 1 and 2.

TABLE III

| Physical Property | Example 1 | Example 2 |
|---|---|---|
| diameter (mm) | 0.286 | 0.306 |
| knob-pull strength (kg) | 2.16 | 2.23 |
| Tensile strength (kg/mm$^2$) | 49.8 | 46.6 |
| Straight-pull strength (kg) | 3.2 | 3.4 |
| Strain energy 0–5% (kg-mm) | 1.24 | 1.48 |
| Strain energy 0–10% (kg-mm) | 5.52 | 5.96 |
| Elongation (%) | 38 | 47 |

COMPARATIVE EXAMPLE

TABLE IV Below sets forth the physical properties of a PDSII suture, which is made from a homopolymer of polydioxanone (commercially available from Ethicon, Inc., Sommerville, N.J).

TABLE IV

| diameter (mm) | 0.308 |
|---|---|
| knot-pull strength (kg) | 2.5 |
| Young's Modulus (kpsi) | 210 |
| Straight-pull strength (kg) | 3.9 |
| Strain energy 0–5% (kg-mm) | 1.83 |
| Strain energy 0–10% (kg-mm) | 6.52 |
| Elongation (%) | 45 |
| Tensile strength (kg/mm$^2$) | 52.9 |

As the data in Tables III and IV illustrate, the suture made of the copolymer of the present invention showed improved flexibility while demonstrating acceptable physical properties, such as knot-pull and straight-pull strength.

EXAMPLE 3

Figure 3A:
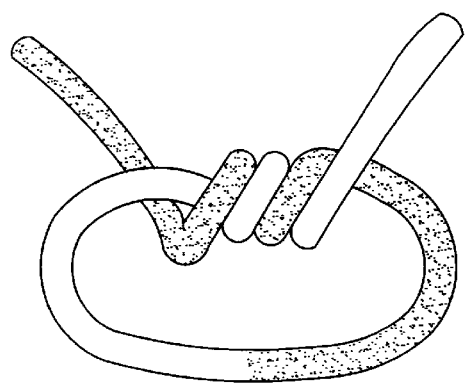
FIGS. 3A–3C illustrate the formation of the knot which was employed in the loop-pull test used in Example 3.
Figure 3B:
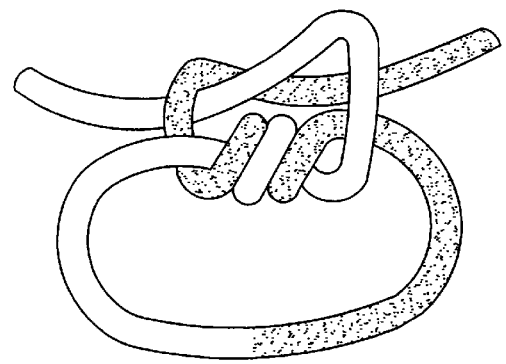
Figure 3C:
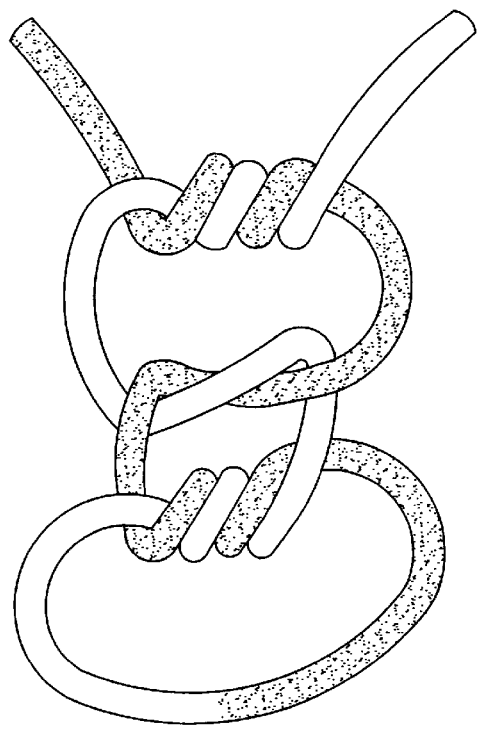

Monofilament sutures manufactured in accordance with the above described process using the copolymer of Example 1 were tested for in vitro strength retention. In vitro loop-pull strength retention is indicative of in vivo strength retention. The in vitro strength retention of the suture was tested as follows:

To simulate in vivo conditions, the suture samples were stored in a container filled with Sorenson's buffer solution at 37° C. After various periods of time, the suture samples were then removed from the container to test their loop-pull strength as follows. A knotted loop was formed in a test suture in three steps as shown in FIGS. 3A–3C. As shown in step 1 of FIG. 3A, each suture was given a double throw (left over right) around a 2 cm diameter cylinder. In Step 2, the free ends of the suture were set in a single throw (right over left) onto, the initial throw of step 1. Finally, in step 3, another double throw (left over right) was set onto the single throw of Step 2 to complete the knot. The free ends of the suture were cut to approximately 0.5 inches and the loop was carefully eased from the cylinder.

Testing of the loop was carried out using an Instron Corporation (Canton, Mass.) Tensile Tester Model No. 4301, operated with a crosshead speed of 25 mm/min and equipped with flat grips, each having a pin over which the loop is positioned.

The results of the tests, are presented in Table V hereinbelow. In the strength retention data reported in Table V, $T_n$ represents the time elapsed in weeks since the sample was placed in the solution, with n representing the number of weeks.

For comparison purposes, the same tests were conducted on a Maxon suture, which is made from a glycolide/glycolide-trimethylene carbonate/glycolide copolymer (commercially available in 1993 from Davis and Geck, Danbury, Conn.); PDSII suture, which is made from polydioxanone homopolymer (commercially available from Ethicon, Inc., Summerville, N.J.); Monocryl suture, which is made from a glycolide/glycolide-caprolactone/glycolide copolymer (commercially available from Ethicon, Inc., Summerville, N.J.). All comparative tests were performed on size 3/0 sutures.

TABLE V

IN VITRO STRENGTH RETENTION.

IN VITRO STRENGTH RETENTION

| COMPOSITION | $T_1$ % | $T_2$ % | $T_3$ % | $T_4$ % | $T_6$ % | $T_8$ % | $T_{10}$ % | $T_{12}$ % |
|---|---|---|---|---|---|---|---|---|
| MAXON | 88 | 81 | 79 | 69 | 33 | — | — | — |
| MONOCRYL | 51 | 21 | 3 | — | — | — | — | — |
| PDSII | — | — | — | 84 | — | 34 | — | 10 |
| VICRYL | 91 | 64 | 35 | — | — | — | — | — |
| EXAMPLE 1 | — | 79 | — | 41 | 28 | 15 | — | — |

As the data in Table V demonstrates, the suture of Example I further exhibits an in vitro strength retention greater than Monocryl and less than Maxon and PDSII.

EXAMPLE 4

Dioxanone (80 grams), trimethylene carbonate (20 grams), were added to a 250 milliliter flask along with 0.0195 grams of stannous octoate and 0.0203 grams of distilled diethylene glycol (DEG). The mixture was dried under vacuum for about 16 hours. The flask was then placed in an oil bath for about 24 hours, with the oil bath temperature set at 100° C., and the reactants stirred with a mechanical stirrer at about 120 revolutions per minute (rpm). Then the temperature was lowered to about 90° C. and the flask was maintained in the oil bath with continued mechanical stirring at about 120 rpm for another 5 hours.

The reaction product was then isolated, comminuted, and treated to remove residual reactants using known techniques. The treatment to remove residual reactants occurred at 75° C. for about 19 hours under vacuum.

The inherent viscosity of the resulting copolymer was taken on a Cannon CT-1000 viscometer (commercially available from Fischer Scientific, Pittsburgh, Pa.). Measurements were taken at 25° C. and 30° C. and at concentrations of 0.1 gram/deciliter (g/dl) and 0.25 (g/dl). The results were as follows:

| Temperature | Concentration | Inherent Viscosity |
|---|---|---|
| 25° C. | 0.1 g/dl | 1.33 g/dl |
| 25° C. | 0.25 g/dl | 1.29 g/dl |
| 30° C. | 0.1 g/dl | 1.28 g/dl |
| 30° C. | 0.25 g/dl | 1.26 g/dl |

Dioxanone (85 grams), trimethylene carbonate (15 grams), were added to a 250 milliliter flask along with 0.0227 grams of stannous octoate and 0.0193 grams of distilled diethylene glycol (DEG). The mixture was dried under vacuum for about 16 hours. The flask was then placed in an oil bath for about 25 hours, with the oil bath temperature set at 100° C., and the reactants stirred with a mechanical stirrer at about 115 revolutions per minute (rpm). The temperature was raised to about 125° C. and the flask was maintained in the oil bath with continued mechanical stirring at about 120 rpm for another 5 hours. Then, the temperature was lowered to about 90° C. with the flask being maintained in the oil bath with continued mechanical stirring at about 120 rpm for another hour.

The reaction product was then isolated, comminuted, and treated to remove residual reactants using known techniques. The treatment to remove residual reactants occurred at 75° C. for about 19 hours under vacuum.

The inherent viscosity of the resulting copolymer was taken on a Cannon CT-1000 viscometer (commercially available from Fischer Scientific, Pittsburgh, Pa.). Measurements were taken at 25° C. and 30° C. and at concentrations of 0.1 gram/deciliter (g/dl) and 0.25 (g/dl). The results were as follows:

| Temperature | Concentration | Inherent Viscosity |
|---|---|---|
| 25° C. | 0.1 g/dl | 1.20 g/dl |
| 25° C. | 0.25 g/dl | 1.16 g/dl |
| 30° C. | 0.1 g/dl | 1.19 g/dl |
| 30° C. | 0.25 g/dl | 1.14 g/dl |

It will be understood that various modifications may be made to the embodiments disclosed herein. Therefore the above description should not be construed as limiting, but merely as exemplifications of preferred embodiments. Those skilled in the art will envision other modifications within the scope and spirit of the claims appended hereto.

What is claimed is:

1. A medical device comprising a suture-needle combination comprising a filament spun from a random copolymer containing at least about 93 mole percent 1,4 dioxane-2-one and 1,3 dioxane-2-one.

2. The device of claim 1 wherein the random copolymer contains about 20 mole percent 1,3 dioxane-2-one.

3. The device of claim 1 wherein the random copolymer possesses an inherent viscosity of about 1.2 to about 2.5 dl/g at 30° C. and a concentration of 0.25 g/dl in hexafluoroisopranol (HFIP).

4. A method of suturing a wound comprising:
  a. providing a needled suture fabricated from a random copolymer comprising at least about 93 mole percent 1,4 dioxane-2-one and 1,3 dioxane-2-one;
  b. passing said needled suture through tissue to create wound closure.

* * * * *